United States Patent [19]

Berkowitz

[11] 4,217,296
[45] Aug. 12, 1980

[54] ALKYL GLYCERYL ETHER SULFATE SALTS AND PROCESS FOR THEIR PREPARATION

[75] Inventor: Sidney Berkowitz, Highland Park, N.J.

[73] Assignee: FMC Corporation, Philadelphia, Pa.

[21] Appl. No.: 960,342

[22] Filed: Nov. 13, 1978

Related U.S. Application Data

[63] Continuation-in-part of Ser. No. 927,183, Jul. 24, 1978, abandoned.

[51] Int. Cl.$^2$ .................... C07C 141/08; C07C 41/02; C07C 43/11
[52] U.S. Cl. ................ 260/458 R; 568/618; 568/679; 568/680; 252/351; 252/353; 252/551
[58] Field of Search .................... 260/458 R; 568/618, 568/680, 679

[56] References Cited

U.S. PATENT DOCUMENTS

| | | | |
|---|---|---|---|
| 1,897,741 | 2/1933 | Ulrich et al. | 260/458 R |
| 2,161,937 | 6/1939 | Scott | 260/458 R |
| 2,255,916 | 9/1941 | Doelling | 260/680 |
| 2,677,700 | 5/1954 | Jackson et al. | 260/458 R |
| 2,989,547 | 6/1961 | Whyte | 568/614 |
| 3,024,273 | 3/1962 | Whyte et al. | 260/458 R |
| 3,350,460 | 10/1967 | Lambert | 568/680 |
| 3,395,170 | 7/1968 | Walts et al. | 260/458 R |
| 3,686,098 | 8/1972 | Well | 260/458 R |
| 3,879,475 | 4/1975 | Wojtowicz et al. | 568/618 |
| 3,928,224 | 12/1975 | Van lerberghe et al. | 568/618 |

FOREIGN PATENT DOCUMENTS

| | | | |
|---|---|---|---|
| 757749 | 6/1954 | Fed. Rep. of Germany | 260/458 R |
| 2657517 | 7/1977 | Fed. Rep. of Germany | 568/680 |
| 1337681 | 8/1963 | France | 568/618 |
| 977281 | 12/1964 | United Kingdom | 260/458 R |

OTHER PUBLICATIONS

Kirk–Othmer, Encyclopedia of Chemical Technology, 2nd edition, vol. 19, pp. 512 and 522–529, 1969.

*Primary Examiner*—Nicky Chan
*Attorney, Agent, or Firm*—Christine M. Miles; Frank Ianno

[57] ABSTRACT

Novel sulfate salts of $C_{10}$–$C_{20}$ linear alkyl glyceryl ether alcohols, useful as biodegradable surfactants in detergent compositions, are prepared by reacting a stoichiometric excess of $C_{10}$–$C_{20}$ linear alkyl alcohol with glycidol predissolved in hexyl acetate, to selectively produce $C_{10}$–$C_{20}$ linear alkyl glyceryl ether alcohols containing 1–3 glyceryl units, sulfating said ether alcohols, and neutralizing the sulfates with base.

23 Claims, No Drawings

ALKYL GLYCERYL ETHER SULFATE SALTS AND PROCESS FOR THEIR PREPARATION

The application is a continuation-in-part of copending application Ser. No. 927,183, filed July 24, 1978.

The present invention relates to anionic surfactants useful in formulating detergent compositions. More particularly, this invention relates to novel sulfate salts of $C_{10}$–$C_{20}$ linear alkyl glyceryl ether alcohols containing 1–3 glyceryl units and to a process for producing the same. The invention further relates to a process for producing $C_{10}$–$C_{20}$ linear alkyl glyceryl ether alcohols used in preparing the compounds of the invention.

In recent years the detergent industry has been increasing its usage of anionic surfactants, particularly the biodegradable aliphatic and/or alicyclic ether sulfate and sulfonate salts.

Certain of these sulfate salts and processes for their preparation are disclosed in West German Pat. No. 757,749, British Patent No. 977,281 and French Pat. No. 1,337,681 (based on the same priority document as the British Patent Specification). The West German patent discloses the preparation of 1,3 di-ethers of glycerol. Sulfate salts are prepared therefrom by reaction of the secondary hydroxyl group with a sulfating agent and neutralization of the sulfate product with base.

The British Patent Specification and the French patent both disclose the preparation of branched $C_8$–$C_{20}$ alkyl ethers of ethylene glycol (formed by reactions involving ethylene glycol or ethylene oxide). More specifically, branching of the $C_8$–$C_{20}$ alkyl radical occurs at the alpha carbon atom which is substituted with at least two alkyl groups. Sulfate salts are prepared therefrom by reacting the primary hydroxyl group of the ethylene glycol moiety in a fashion similar to that described above.

The French patent additionally describes the preparation of sulfate salts of similarly branched alkyl ether alcohols containing 1–3 ethylene oxide units. Further, Example VII of this patent describes the reaction of glycerol and dodecene-1 to produce a mixture of branched alkyl ether alcohols. Branched alkyl sulfate salts of the type disclosed by the British and French patents, however, are less readily biode-graded than the analogous linear alkyl (unbranched n-alkyl) sulfate salts.

Certain alkyl ether sulfonate salts and their preparation are described in U.S. Pat. No. 3,024,273, to D. D. Whyte et al. Specifically, there is disclosed the preparation of $C_8$–$C_{22}$ alkyl chloroglyceryl ethers having 1–4 glyceryl units by reacting a stoichiometric excess of epichlorohydrin with high molecular weight fatty alcohols in the presence of a catalyst (polymerization when occurring, being primarily via an oxygen on the middle carbon of the glyceryl unit). The sulfonate salts are prepared therefrom by reacting at least one chlorine atom in the molecule with sodium or potassium sulfite. Sulfonation of chlorinated compounds, however, generally requires harsher conditions than sulfation of alcohols and the former is consequently more costly than the latter, particularly in terms of energy and equipment.

Regarding the preparation of aliphatic glyceryl ether alcohols, it is known that certain of such compounds may be prepared by reacting the corresponding aliphatic alcohol with glycidol. West German Pat. No. 2,657,517, to K. L. Jones broadly discloses that mono-glyceryl ethers of alkanols may be prepared by condensation of a higher alkanol with glycidol.

J. A. Wojtowicz et al, in U.S. Pat. No. 3,719,636, disclose a process for preparing $C_8$–$C_{26}$ aliphatic glyceryl ether alcohols containing 4–14 glyceryl units.

The process involves reacting glycidol and the selected aliphatic alcohol, in a molecular ratio within the range of 4:1 to 14:1 respectively. The reaction is carried out in the presence of an acid or base catalyst, and a solvent which is polar, nonreactive, and miscible with the selected alcohol, glycidol and reaction product. Specific solvents disclosed as being suitable in carrying out the process are ketones, ethers, amides, and dioxolanes, the choice of the particular solvent depending upon the choice of catalyst. The process, however, does not provide for the selective production of linear alkyl glyceryl ether alcohols containing 1–3 glyceryl units required for the preparation of the corresponding sulfate salts of the present invention.

A new composition of matter has been found which consists essentially of a mixture of sulfated alkyl mono- and poly-glyeryl ether alcohol compounds of the general formula:

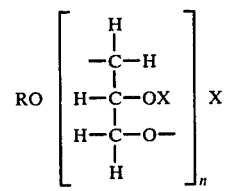

wherein R is a linear alkyl radical (an n-alkyl radical free of branching) containing from about 10 to about 20 carbon atoms, n is an integer from 1 to 3, and X is selected from the group consisting of hydrogen and sulfonic acid salt radicals, at least one X in each compound of the mixture being a sulfonic acid salt radical. Said mixture preferably contains a major proportion of such sulfated alkyl glyceryl ether alcohols where n is 1, the balance of said mixture consisting predominately of a mixture of such sulfated alkyl glyceryl ether alcohols where n is 2 and 3. In preparing the sulfated mixture of the invention, a precursor linear alkyl glyceryl ether alcohol mixture is prepared by a process which comprises of steps of: bringing together and reacting a $C_{10}$–$C_{20}$ linear alkyl alcohol and glycidol which is predissolved in hexyl acetate, in the presence of an acid catalyst in a reaction zone, said alcohol and glycidol being brought together and reacted in a molecular ratio within the range of from about 1.5:1 to about 8:1; maintaining the resulting reaction mass in an agitated condition; maintaining the temperature of the reaction mass within the range of from about 25° to about 125° C. during the reaction period, and recovering a mixture of linear alkyl glyceryl ether alcohols containing 1 to 3 glyceryl units from the reaction mass. The sulfated mixture is prepared by contacting and reacting said mixture of ether alcohols with a sulfating agent, said ether alcohols and sulfating agent being contacted and reacted in a molecular ratio within the range of from about 1:1 to about 1:1.15; maintaining the resulting sulfation reaction mass in an agitated condition; maintaining the temperature of the sulfation reaction mass within the range of from about −15° to about 75° C. during the reaction period; recovering a mixture of linear alkyl glyceryl ether alcohol sulfates, neutralizing said mixture of sulfates with base and recovering a mixture of linear alkyl glyceryl ether sulfate salts containing 1 to 3 glyceryl units.

Preparation of the $C_{10}$–$C_{20}$ linear alkyl glyceryl ether sulfate salts of the invention involves the initial preparation of $C_{10}$–$C_{20}$ linear alkyl glyceryl ether alcohols, containing 1–3 glyceryl units. The formation of these ether alcohols in the process of the invention may be said to progress stepwise in accordance with the following equations, wherein R is a linear alkyl radical containing from about 10 to about 20 carbon atoms and preferably 12 to 16 carbon atoms:

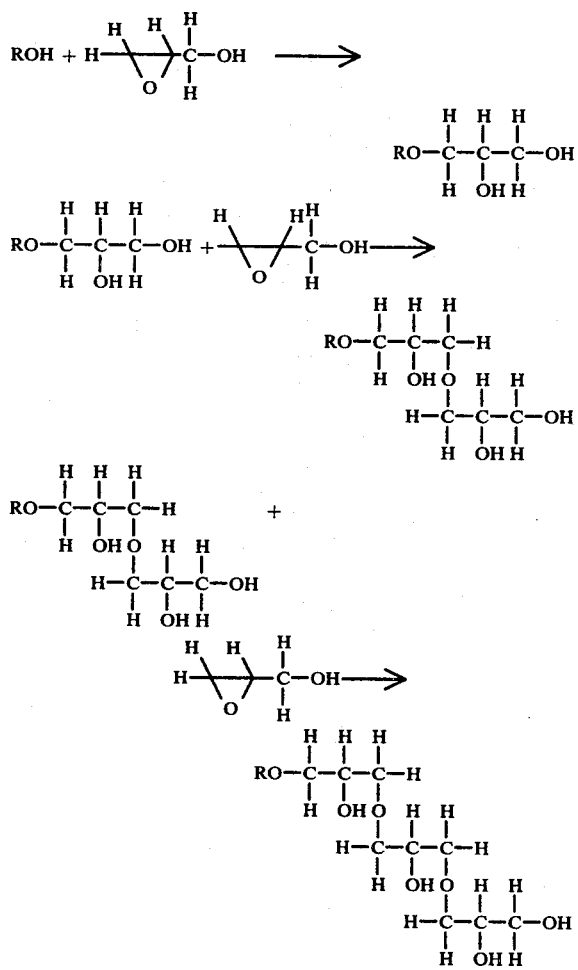

The mixture of alkyl glyceryl ether alcohols thus formed can be represented by the following general formula:

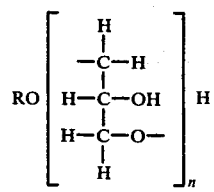

wherein R is a linear alkyl radical containing from about 10 to about 20 carbon atoms and preferably 12 to 16 carbon atoms, n is an integer from 1 to 3, said mixture containing a major proportion of such ether alcohols wherein n is 1. For convenience of description, the linear alkyl glyceryl ether alcohols wherein n is 1, 2 or 3, will hereinafter also be referred to respectively as the monomer, dimer and trimer ether alcohols.

The aforesaid mixture of monomer, dimer and trimer ether alcohols will contain positional isomers of the various glyceryl ether alcohols, and it is to be understood that herein and in the appended claims, any reference to the glyceryl ether alcohols, or corresponding sulfate salts, is to be construed as including within its scope the positional isomers of said glyceryl ether alcohols. For example, the epoxy ring of the glycidol may break so that the ether linkage between the alcohol and glyceryl radical may attach to either the terminal or middle carbon of the glyceryl radical. Also, the attachment of the second glyceryl radical to the first may be through an ether linkage to the terminal or middle carbon atom. By way of illustration, four of the isomeric di-glyceryl ether alcohols may be illustrated by the following structural formulations:

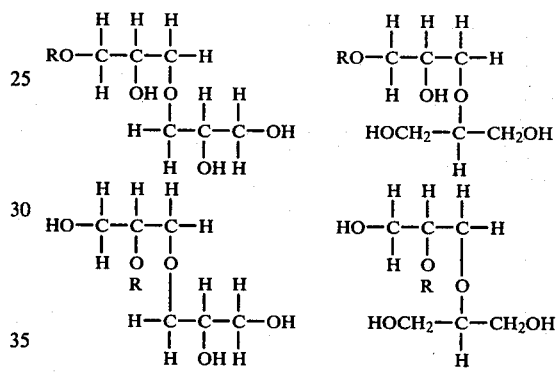

In preparing the alkyl glyceryl ether alcohols in accordance with the process of the invention, at least 1.5 moles of $C_{10}$–$C_{20}$ linear alkyl alcohol are used for every one mole of glycidol which is to be reacted, for example, at least 50% excess $C_{10}$–$C_{20}$ linear alkyl alcohol over the stoichiometric equivalent of glycidol is used. It has been found that use of such excess of alkyl alcohol is critical in obtaining good product yields, that is, typically 90% or more, based on the starting glycidol. Use of stoichiometric equivalents of reactants for example produces a product which is predominately higher molecular weight polyglyceryl materials. Accordingly, molecular ratios of alkyl alcohol to glycidol within the range of from about 1.5:1 to about 8:1 are preferred. Optimum conversions to product with optimum utilization of alkyl alcohol reactant are obtained at alkyl alcohol to glycidol ratios within the range of from about 2:1 to about 4:1. As might be expected, increasing amounts of dimer and trimer ether alcohols are formed by employing decreasing proportions of alkyl alcohol reactant.

Hexyl acetate is used as the solvent in the process of the invention. It has been found that this solvent selectively dissolves the desired monomer, dimer and trimer ether alcohol reaction products while throwing out of solution, higher molecular weight polyglyceryl materials which could be formed if, for example, the rate of glycidol addition to the alkyl alcohol reactant was greater than that for optimum product yield, and/or the degree of agitation of the reaction mass was less than that for optimum product yield. This solvent thus operates to concentrate the monomer, dimer and trimer ether alcohols therein, facilitating isolation of said compounds.

The glycidol reactant is dissolved in the hexyl acetate prior to its being contacted and reacted with the alkyl alcohol. The concentration of glycidol in hexyl acetate although not critical, is preferably from about 2 to about 30 weight %, the most preferred range being from about 7 to about 20 weight %.

The catalyst used in preparing the monomer, dimer and trimer ether alcohols can be any of the Lewis type acids which are known to be active in Friedel-Crafts type reactions. Suitable catalysts of this nature include for example $BF_3.Et_2O$, $SnCl_4$, $TiCl_4$, $SbCl_3$, HF, $AlCl_3$, $SeCl_3$, $ZnCl_2$ and $ZnBr_2$, with the preferred catalyst embodiment being the $SnCl_4$.

The amount of catalyst used will generally vary from 0.5 to 10% based on the amount of selected linear alkyl alcohol employed and preferably will vary from 0.5 to 3%.

The temperature at which the glycidol/alkyl alcohol reaction is carried out will generally vary from 25° to 125° C., and preferably from 60° to 95° C.

Preferably, this reaction is carried out under an inert atmosphere, for example, a nitrogen atmosphere, to prevent undesired glycidol polymerization and to prevent moisture in the air from deactivating the acid catalyst.

Means are provided for maintaining the reaction mass in an agitated condition throughout the reaction period to facilitate contact between the reactants. Preferably, the degree of agitation provided is selected in coordination with the rate of addition of glycidol to the reaction zone so as to minimize the presence of isolated concentrations of glycidol in the reaction zone which can lead to formation of undesired higher molecular weight polymeric materials.

The reaction time for obtaining good yields of monomer, dimer and trimer ether alcohols can vary from about 0.5 to about 4 hours, but is genrally from about 1 to about 2 hours, the time being primarily a function of the selected reaction temperature and the degree of agitation provided.

At the end of the reaction period, the reaction mass is preferably washed with a sufficient amount of water to deactivate the catalyst. When such procedure is employed, the organic phase is then separated from the aqueous phase and any insolubles, for example, polyglyceryl materials, by any of the well known means for effecting such separation, for example, decantation and the like.

The organic phase is subjected to distillation to remove the hexyl acetate solvent and any unreacted alkyl alcohol or glycidol which may be present. Remaining, is a mixture consisting essentially of the monomer, dimer and trimer ether alcohols, the monomer ether alcohol comprising a major proportion of the mixture.

If desired, the mixture of monomer, dimer and trimer ether alcohols can be subjected to a further distillation whereby a fraction consisting of essentially pure monomer and a fraction comprising a major proportion of dimer with up to about 3 weight % trimer are readily separated. The mixture of monomer, dimer and trimer ether alcohols or any of the distillation fractions can be sulfated as hereinafter described.

The products of the invention which result from sulfation of the aforementioned mixture of ether alcohols or distillate fractions thereof can be represented by the following general formula:

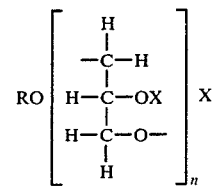

wherein R is a linear alkyl radical containing from about 10 to about 20 carbon atoms and preferably 12 to 16 carbon atoms, n is an integer from 1 to 3, and X is selected from the group consisting of hydrogen and sulfonic acid salt radicals, at least one X in the product being a sulfonic acid salt radical, the cation of said sulfonic acid salts being selected from the group consisting of sodium, potassium, ammonium, tetra-alkyl ammonium, and alkylol substituted ammonium in which the alkylol contains a whole number of carbon atoms from 2 to 3.

When the mixture of ether alcohols from the glycidol/alkyl alcohol reaction is sulfated and neutralized directly, without separating or concentrating any particular component or components, the resulting sulfate salt mixture contains a major proportion of such sulfated salts where n is 1, the balance of said mixture consisting predominately of a mixture of such sulfated salts where n is 2 and 3. Generally said mixture contains at least 80% of such sulfated ether alcohols wherein n is 1.

In carrying out the sulfation reaction, the alkyl glyceryl ether alcohol reactant is contacted and reacted with a sulfating agent. Any of the known sulfating agents, such as chlorosulfonic acid, sulfur trioxide, pyrosulfate, oleum and sulfuric acid can be used in the process of the invention, the preferred sulfating agents being chlorosulfonic acid and sulfur trioxide.

Generally, molecular ratios of alkyl glyceryl ether alcohol to sulfating agent within the range of from about 1:1 to about 1:1.15 respectively are satisfactory in carrying out the sulfation reaction. When chlorosulfonic acid or sulfur trioxide is employed as the sulfating agent, the preferred molecular ratio of ether alcohol reactant to sulfating agent is within the range of from about 1:1.01 to about 1:1.05 respectively.

Such molecular ratios provide a product containing at least about one sulfate group per molecule. When stoichiometric ratios are employed, there is on the order of one sulfate group per molecule, primarily on an end carbon of the glyceryl unit. When a stoichiometric excess of sulfating agent (within the above range) is employed, up to about 1.0% by weight of the product may comprise compounds having more than one sulfate group per molecule.

Preferably the ether alcohol reactant is predissolved in an inert diluent prior to being contacted with the sulfating agent. This procedure minimizes localized overheating in the reaction mass which may occur during admixture of the reactants. Such overheating can cause undesirable side reactions and decomposition of the alkyl chain, resulting in decreased yields and discoloration of the product.

Suitable inert diluents for predissolving the ether alcohol include organic solvents as the chlorinated methanes or ethanes, and 1,4-dioxane and the like. The preferred diluent is methylene chloride since it provides relatively concentrated solutions of the alkyl glyceryl ether alcohol reactant, for example, on the order of 30 weight percent, which allow for more rapid and complete sulfation than less concentrated solutions. Further, the relatively low boiling point of this diluent permits it to function as a built-in heat sink for controlling the reaction temperature, and permits its ready removal from the product upon completion of the reaction.

The concentration of alkyl glyceryl ether alcohol reactant in the selected diluent may vary, although as stated above, relatively concentrated solutions are preferred. Concentrations within the range of from about 10 weight percent to about 80 weight percent may be employed, the preferred range being from about 25 weight percent to about 50 weight percent.

When sulfur trioxide is employed as the sulfating agent it is additionally preferred to employ a diluent for this reactant. Such procedure minimizes product decomposition which might result from high concentrations of sulfur trioxide in the reaction mass. The diluent for sulfur trioxide should be inert to the materials in the reaction mass at the conditions employed, and is admixed with the sulfur trioxide prior to being contacted with the ether alcohol reactant.

Suitable diluents for the sulfur trioxide include for example nitrogen, air and sulfur dioxide, the amount of diluent being preferably sufficient to prevent or minimize said product decomposition.

Means are provided for maintaining the reaction mass in an agitated condition throughout the sulfation reaction period to facilitate contact between the reactants and to minimize or prevent localized overheating in the reaction mass during admixture of the reactants.

The temperature at which the sulfation reaction is carried out will generally vary from about $-15°$ to about 75° C. When chlorosulfonic acid is employed as the sulfating agent, the reaction temperature is preferably within the range of 30° to 40° C. When sulfur trioxide is employed as the sulfating agent, the reaction temperature is preferably within the range of $-10°$ to 20° C.

The reaction time for preparing the products of the invention is primarily a function of reaction temperature, the particular diluent, and the sulfating agent. Generally, reaction times are on the order of minutes. When, for example, methylene chloride is employed as the diluent, and chlorosulfonic acid as the sulfating agent, reaction times between 5-10 minutes are generally sufficient at reaction temperatures within the preferred range for this sulfating agent.

When chlorosulfonic acid is employed as the sulfating agent, it is preferable, after completion of the reaction, to maintain the reaction mass at the reaction temperature for an additional time sufficient to drive off any remaining hydrogen chloride formed during the reaction period. Such additional time is typically about 2 minutes.

After completion of the sulfation reaction and any further heating to remove hydrogen chloride, the sulfate product is recovered upon removal from the reaction mass (generally by distillation at reduced pressure) of any diluents employed.

In neutralizing the sulfate product to produce the linear alkyl glyceryl ether sulfate salts of the invention, sufficient water is added to dissolve at least some and preferably all of the sulfate product. The resulting solution (or slurry) is contacted with a base selected from the group consisting of sodium hydroxide, potassium hydroxide, ammonia, ammonium hydroxide, tetra-alkyl ammonium hydroxide, and alkylolsubstituted ammonia in which the alkylol contains a whole number of carbon atoms from 2 to 3, the amount of base being sufficient to raise the pH of the solution to a value within the range of from about 6.5 to about 8.5.

The linear alkyl glyceryl ether sulfate salts of the invention are recovered upon drying the resulting solution or slurry.

The following examples are given to illustrate the invention and are not intended to be limiting thereof.

EXAMPLE I

This example demonstrates the production of a mixture of lauryl mono-, di- and tri-glyceryl ether alcohols (that is, monomer, dimer and trimer ether alcohols) and the isolation of essentially pure monomer therefrom.

Seventy-four and four-tenths grams (0.4 moles) of lauryl alcohol were charged to a 250 ml 3-necked round-bottom glass reaction flask equipped with a thermometer, Teflon ® paddle stirrer, condenser and pressure-equalizing dropping funnel. Nine-tenths of a gram of stannic chloride catalyst were added to the lauryl alcohol and the solution was heated to 60° C. A solution of 14.8 grams (0.2 moles) of glycidol in 100 ml hexyl acetate (16.6 weight percent glycidol solution) was added dropwise to the contents of the flask over a 25-30 minute period. A nitrogen blanket was maintained over the resulting reaction mass throughout the reaction period. The reaction was mildly exothermic and the temperature was allowed to rise to 80° C. during the glycidol addition. After completion of the glycidol addition, the reaction temperature was increased to 90° C. and the reaction mass was stirred at that temperature for 1 hour, then cooled to room temperature. The cooled reaction mass was washed with 25 ml of water to deactivate the catalyst. The resulting organic phase was separated by decantation and subjected to distillation. After distillation of the lower boiling hexyl acetate and lauryl alcohol, 35.9 grams of essentially pure lauryl mono-glyceryl ether alcohol were separated by distillation at 3 mm Hg. This corresponds to a yield of 69.0% based on the starting glycidol. The undistilled residue from the organic phase contained 9.4 grams of lauryl diglyceryl ether alcohol and 0.3 grams lauryl tri-glyceryl ether alcohol. Thus, a total yield of 99.1% of ether alcohol products, that is, monomer, dimer and trimer, was obtained.

EXAMPLE II

This example demonstrates the production of a mixture of myristyl mono-, di- and tri-glyceryl ether alcohols (that is, monomer, dimer and trimer ether alcohols) and the isolation of the essentially pure monomer therefrom.

The procedure and equipment employed in this example were the same as in Example I. Eighty-five and seventy-five hundredths grams (0.4 moles) of myristyl alcohol were reacted in the presence of 0.9 grams of stannic chloride catalyst with 14.8 grams (0.2 moles) of glycidol dissolved in 100 ml of hexyl acetate. After completion of the reaction, the cooled reaction mass was washed, and the organic phase separated and distilled as described in Example I. Thirty-seven and nine-tenths grams of essentially pure myristyl mono-glyceryl ether alcohol were separated by distillation at 3 mm Hg. This corresponds to a yield of 65.8% based on the starting glycidol. The undistilled residue of the organic phase contained 10.8 grams of myristyl di-glyceryl ether alcohol and 0.5 grams of myristyl tri-glyceryl ether alcohol. Thus, a total yield of 98.5% of ether alcohol products, that is, monomer, dimer and trimer, was obtained.

EXAMPLE III

This example demonstrates the production of a mixture of cetyl mono-, di- and tri-glyceryl ether alcohols (that is, monomer, dimer and trimer ether alcohols) and the isolation of the essentially pure monomer therefrom.

The procedure and equipment employed in this example were the same as in Example I. Ninety-seven grams (0.4 moles) of cetyl alcohol were reacted in the presence of 0.9 grams of stannic chloride catalyst with 14.8 grams (0.2 moles) of glycidol dissolved in 100 ml of hexyl acetate. After completion of the reaction, the cooled reaction mass was washed, and the organic phase separated and distilled as described in Example I. Forty-one and one-tenth grams of essentially pure cetyl mono-glyceryl ether alcohol were separated by distillation at 5 mm Hg. This corresponds to a yield of 65.0% based on the starting glycidol. The undistilled residue of the organic phase contained 11.9 grams of cetyl di-glyceryl ether alcohol, and 0.5 grams of cetyl tri-glyceryl ether alcohol. Thus, a total yield of 98.0% of ether alcohol products, that is, monomer, dimer and trimer was obtained.

EXAMPLE IV

This example demonstrates the importance of employing a stoichiometric excess of linear alkyl alcohol reactant in the process and, the ability of hexyl acetate to throw out of solution higher molecular weight polyglyceryl materials which may be formed.

The procedure and equipment employed in this example were the same as in Example I. Thirty-seven and two-tenths grams (0.2 moles) of lauryl alcohol were reacted in the presence of 0.90 grams of stannic chloride catalyst with 14.8 grams (0.2 moles) of glycidol in 100 ml of hexyl acetate. During admixture of the reactants, a white semi-solid polymeric material, insoluble in the hexyl acetate solvent, began to form. The reaction mass was washed, and the soluble organic phase separated and distilled as described in Example I. The total yield of lauryl mono-, di- and tri-glyceryl ether alcohols was only 29.9%, based on the starting glycidol. The solids insoluble in hexyl acetate were identified by gas chromatographic analysis as higher molecular weight polyglyceryl materials.

EXAMPLE V

This example is intended to demonstrate the insolubility in hexyl acetate of prior art glycidol/aliphatic alcohol adducts having a higher molecular weight than the desired 1-3 glyceryl unit ether alcohols produced by the process of the invention.

A 12 to 1 mole adduct of glycidol to Alfol 1214 (mixture of 55% $C_{12}$ and 43% $C_{14}$ linear aliphatic alcohols produced by Continental Oil Co.) was prepared following the prior art procedure described in Example I of U.S. Pat. No. 3,719,635. Ten grams of the adduct thus prepared were slurried in 250 ml of hexyl acetate at a temperature of 75° C. for 3 hours. The adduct did not appear to be miscible in or to dissolve in the hexyl acetate. Upon cooling to room temperature, the mixture was filtered. Analyses of the hexyl acetate filtrate by mass spectrometry and gas chromatography showed that no detectable amounts of adduct were present therein.

EXAMPLE VI

This example demonstrates the production of essentially pure lauryl mono-glyceryl ether sulfate, potassium salt, that is, monomer ether sulfate, potassium salt.

Forty-one and six-tenths grams (0.16 moles) of lauryl mono-glyceryl ether alcohol prepared and isolated as described as in Example I and 150 ml of methylene chloride were charged to a 500 ml 3-necked round-bottom glass reaction flask equipped with a thermometer, Teflon ® paddle stirrer, condenser and dropping funnel. The ether alcohol readily dissolved in the methylene chloride and the solution was heated to 35° C. Nineteen and twelve-hundredths grams (0.168 moles) of chlorosulfonic acid sulfating agent were added to the contents of the flask over a 5-minute period. Evolution of hydrogen chloride from the resulting reaction mass began immediately upon addition of the sulfating agent. The reaction was initially exothermic, tne temperature rising to 40° C. After about one-half of the sulfating agent was added, external heat was applied to maintain the reaction temperature at 40° C. (reflux temperature). The reaction mass was refluxed for an additional 2 minutes after addition of the sulfating agent was completed. The methylene chloride solvent was then stripped from the reaction mass at reduced pressure (25 mm Hg), leaving a colorless, waxy solid residue in the reaction flask. One hundred and fifty ml of water were added to the residue in the flask. The resulting mixture, which had a pH of 1.3, was neutralized to a pH of 8.0 by addition of 25% potassium hydroxide. A thick slurry was obtained which upon drying produced 60.6 grams of a white free-flowing solid. This solid assayed as 99% pure lauryl mono-glyceryl ether sulfate, potassium salt, which corresponds to a 99.2% yield based on starting lauryl mono-glycerol ether alcohol.

EXAMPLE VII

This example demonstrates the production of essentially pure lauryl mono-glyceryl ether sulfate, sodium salt, that is, monomer ether sulfate, sodium salt.

The chemicals, procedure and equipment employed in this example are the same as in Example VI, except that neutralization was effected with 25% sodium hydroxide. Upon drying of the resultant slurry, 58.5 grams of a thick free-flowing solid were obtained. This solid assayed as 98% pure lauryl mono-glyceryl ether sulfate, sodium salt, which corresponds to a 99.0% yield based on starting lauryl mono-glyceryl ether alcohol.

EXAMPLE VIII

This example demonstrates the production of essentially pure lauryl mono-glyceryl ether sulfate, ammonium salt, that is, monomer ether sulfate, ammonium salt.

The chemicals, procedure and equipment employed in this example are the same as in Example VI, except that neutralization was effected with 20% ammonium hydroxide. Upon drying of the resultant slurry, 57.7 grams of a thick, wax-like solid were obtained. This solid assayed as 98% pure lauryl mono-glyceryl ether sulfate, ammonium salt, which corresponds to a 99.0% yield based on starting lauryl mono-glyceryl ether alcohol.

EXAMPLE IX

This example demonstrates the production of lauryl di-glyceryl ether sulfate, potassium salt, that is, dimer ether sulfate, potassium salt, together with a small amount of the corresponding trimer sulfate salt.

The chemicals, procedure and equipment employed in this example were the same as in Example VI, except that the glyceryl ether alcohol reactant was lauryl di-glyceryl ether alcohol (containing about 2% by weight lauryl tri-glyceryl ether alcohol) obtained by a further distillation of the residue from the organic phase produced as described in Example I. Ten and two hundredths grams (0.03 moles) of such ether alcohol reactant were sulfated in 50 ml methylene chloride with 3.63 grams (0.0312 moles) of chlorosulfonic acid. After completion of the reaction, the methylene chloride solvent was stripped from the reaction mass and 25 ml water added to the residue as described in Example VI. Neutralization to a pH of 8 was effected by addition of 25% potassium hydroxide. Upon drying the resulting slurry, 13.8 grams of a white free-flowing solid were obtained. This solid assayed as 97.6% dimer and trimer lauryl glyceryl ether sulfates, potassium salts, (the trimer being present in only a few percent) which corresponds to a 99.3% yield based on starting lauryl di-glyceryl ether alcohol reactant.

EXAMPLE X

This example demonstrates the production of a mixture of lauryl mono-, di- and tri-glyceryl ether sulfates, potassium salts, that is, monomer, dimer and trimer glyceryl sulfates, potassium salts.

A mixture of lauryl glyceryl ether alcohols comprising approximately 90 weight % monomer, 10 weight % dimer, and 0.1 weight % trimer ether alcohols was prepared following the procedure described in Example I. The equipment and procedure employed in preparing the ether sulfates, potassium salts, in this example were the same as in Example VI. 45.3 grams (0.16 moles) of the ether alcohol mixture dissolved in 150 ml of methylene chloride were reacted with 20.15 grams (0.1729 moles) of chlorosulfonic acid sulfating agent. After completion of the reaction, the methylene chloride diluent was stripped from the reaction mass and 175 ml water added to the residue as described in Example VI. Neutralization to a pH of 8.1 was effected by addition of 25% potassium hydroxide. Upon drying of the resultant slurry, 64.3 grams of a white free-flowing solid were obtained. This solid assayed as 99% monomer, dimer and trimer lauryl glyceryl ether sulfates, potassium salts, which corresponds to a 99.2% yield based on the starting lauryl glyceryl ether alcohol mixture.

EXAMPLE XI

This example is intended to demonstrate the detersive properties of the glyceryl ether sulfate salts of the invention.

Surface tension, foam height and foam half-life measurements were made on the glyceryl ether sulfate salts obtained from Examples VI, VII, VIII, IX and X. The same measurements were made using lauryl sulfate sodium salt, which is used by the industry as a standard for comparing the detersive properties of anionic sulfate surfactants.

The surface tension measurements were made using a Fisher Surface Tensiometer and are reported in Table I as dynes/cm at 23.5° C. Low values for this measurement are indicative of good detersive action. As can be seen from the table, values for the compounds of the invention are on the order of 40% lower than the value for the standard, lauryl sulfate, sodium salt.

The foam height and foam half-life measurements were made following the Ross Miles Test (ASTM Method D 1173-53). Values for these measurements are given in Table I. High values are desired as they are indicative of good foam stability. As can be seen from the table, foam height (initial and after five minutes) and foam half-life values for the compounds of the invention are in all instances appreciably greater than the corresponding values for the standard, lauryl sulfate, sodium salt.

This invention being thus described, it will be obvious that the same may be varied in many ways. Such variations are not to be regarded as a departure from the spirit and scope of the invention, and all such modifications are intended to be included within the scope of the following claims.

TABLE 1
DETERSIVE PROPERTIES OF LAURYL GLYCERYL ETHER SULFATE SALTS

| Compound (0.1% Aqueous Solution) | Compound Source | Surface Tension (23.5° C.) Dynes/cm |
|---|---|---|
| Lauryl sulfate, Na salt | Commercial Standard | 49.4 |
| Lauryl mono-glyceryl ether sulfate, K salt | Example VI | 29.0 |
| Lauryl mono-glyceryl ether sulfate, Na salt | Example VII | 29.0 |
| Lauryl mono-glyceryl ether sulfate, ammonium salt | Example VIII | 28.8 |
| Lauryl di-glyceryl ether sulfate, K salt (with a few percent of corresponding trimer sulfate salt | Example IX | 29.6 |
| Mixture of lauryl, mono-, di- and tri-glyceryl ether sulfates, K salts | Example X | 29.1 |

| | Ross Miles Test ASTM D 1173-53 | |
|---|---|---|
| Compound (0.1% Aqueous Solution | Foam Height (mm) Initial / Aft. 5 min. | Foam Half-Life (min.) |
| Lauryl sulfate, Na salt | 155 / 150 | 11.5 |
| Lauryl mono-glyceryl ether sulfate, K salt | 187 / 184 | 16.7 |
| Lauryl mono-glyceryl ether sulfate, Na salt | 187 / 181 | 19.0 |
| Lauryl mono-glyceryl ether sulfate, ammonium salt | 187 / 184 | 19.4 |
| Lauryl di-glyceryl ether sulfate, K salt (with a few percent of corresponding trimer sulfate salt | 198 / 193 | 17.2 |
| Mixture of lauryl, mono-, di- and tri-glyceryl ether sulfates, K salts | 190 / 188 | 19.8 |

I claim:

1. A process for preparing a mixture of linear alkyl glyceryl ether alcohols containing 1 to 3 glyceryl units which comprises the steps of bringing together and reacting, a $C_{10}$–$C_{20}$ linear alkyl alcohol and glycidol which is predissolved in hexyl acetate, in the presence of an acid catalyst in a reaction zone, said alcohol and glycidol being brought together and reacted in a molecular ratio within the range of from about 1.5:1 to about 8:1; maintaining the resulting reaction mass in an agitated condition; maintaining the temperature of the reaction mass within the range of from about 25° to about 125° C. during the reaction period; and recovering said mixture of linear alkyl glyceryl ether alcohols from the reaction mass.

2. The process of claim 1 wherein the linear alkyl alcohol reactant is a $C_{12}$–$C_{16}$ linear alkyl alcohol.

3. The process of claim 1 wherein the linear alkyl alcohol reactant is lauryl alcohol.

4. The process of claim 1 wherein the linear alkyl alcohol and glycidol are brought together and reacted in a molecular ratio within the range of from about 2:1 to about 4:1.

5. The process of claim 1 wherein the temperature of the reaction mass is maintained within the range of from about 60° to about 95° C.

6. The process of claim 1 wherein the reaction of the linear alkyl alcohol and glycidol is carried out in an inert atmosphere.

7. The process of claim 1 wherein the hexyl acetate solution of glycidol is a 2–30 weight % solution.

8. A process for preparing a mixture of linear alkyl glyceryl ether sulfate salts containing 1 to 3 glyceryl units which comprises the steps of bringing together and reacting, a $C_{10}$–$C_{20}$ linear alkyl alcohol and glycidol wich is predissolved in hexyl acetate, in the presence of an acid catalyst in a reaction zone, said alcohol and glycidol being brought together and reacted in a molecular ratio within the range of from about 1.5:1 to about 8:1; maintaining the resulting reaction mass in an agitated condition; maintaining the temperature of the reaction mass within the range of from about 25° to about 125° C. during the reaction period, recovering a mixture of linear alkyl glyceryl ether alcohols containing 1 to 3 glyceryl units from the reaction mass, contacting and reacting said mixture of ether alcohols with a sulfating agent, said ether alcohols and sulfating agent being contacted and reacted in a molecular ratio within the range of from about 1:1 to about 1:1.15; maintaining the resulting sulfation reaction mass in an agitated condition; maintaining the temperature of the sulfation reaction mass within the range of from about −15° to about 75° C. during the reaction period; recovering a mixture of linear alkyl glyceryl ether sulfates, neutralizing said mixture of sulfates with base and recovering a mixture of linear alkyl glyceryl ether sulfate salts containing 1 to 3 glyceryl units.

9. The process of claim 8 wherein the linear alkyl alcohol reactant is a $C_{12}$–$C_{16}$ linear alkyl alcohol.

10. The process of claim 8 wherein the linear alkyl alcohol reactant is lauryl alcohol.

11. The process of claim 8 wherein the linear alkyl alcohol and glycidol are brought together and reacted in a molecular ratio within the range of from about 2:1 to about 4:1.

12. The process of claim 8 wherein the linear alkyl alcohol and glycidol reaction mass is maintained at a temperature of from about 60° to about 95° C. during the reaction period.

13. The process of claim 8 wherein the reaction between the linear alkyl alcohol and glycidol is carried out under an inert atmosphere.

14. The process of claim 8 wherein the hexyl acetate solution of glycidol is a 2–30 weight % solution.

15. The process of claim 8 wherein the sulfating agent is chlorosulfonic acid.

16. The process of claim 15 wherein the ether alcohols and sulfating agent are contacted and reacted in a molecular ratio within the range of from about 1:1.01 to about 1:1.05.

17. The process of claim 15 wherein the sulfation reaction mass is maintained at a temperature within the range of from about 30° to about 40° C.

18. The process of claim 8 wherein the sulfating agent is sulfur trioxide.

19. The process of claim 18 wherein the sulfur trioxide is admixed with a diluent selected from the group consisting of nitrogen, air and sulfur dioxide, prior to being contacted with the ether alcohol reactant.

20. The process of claim 18 wherein the ether alcohols and sulfating agent are contacted and reacted in a molecular ratio within the range of from about 1:1.01 to about 1:1.05.

21. The process of claim 18 wherein the sulfation reaction mass is maintained at a temperature within the range of from about −10° to about 20° C.

22. The process of claim 8 wherein the ether alcohol is predissolved in a diluent prior to being contacted and reacted with the sulfating agent.

23. The process of claim 22 wherein the diluent is methylene chloride.

* * * * *